United States Patent
Hidalgo et al.

(10) Patent No.: US 11,844,928 B2
(45) Date of Patent: Dec. 19, 2023

(54) SYRINGE PUMP WITH FLANGE CLAMP SENSOR

(71) Applicant: CareFusion 303, Inc., San Diego, CA (US)

(72) Inventors: Ronald Hidalgo, Limerick (IE); Andrei Reaboi, Limerick (IE)

(73) Assignee: CareFusion 303, Inc., San Diego, CA (US)

( * ) Notice: Subject to any disclaimer, the term of this patent is extended or adjusted under 35 U.S.C. 154(b) by 430 days.

(21) Appl. No.: 16/941,384

(22) Filed: Jul. 28, 2020

(65) Prior Publication Data
US 2021/0030948 A1   Feb. 4, 2021

Related U.S. Application Data

(60) Provisional application No. 62/879,950, filed on Jul. 29, 2019.

(51) Int. Cl.
*A61M 5/145* (2006.01)

(52) U.S. Cl.
CPC ... *A61M 5/1458* (2013.01); *A61M 2205/3327* (2013.01); *A61M 2205/6036* (2013.01)

(58) Field of Classification Search
CPC ............ A61M 2205/14; A61M 5/1456; A61M 5/1458
See application file for complete search history.

(56) References Cited

U.S. PATENT DOCUMENTS

| | | | | |
|---|---|---|---|---|
| 2003/0229311 | A1* | 12/2003 | G. Morris | A61M 5/1458 604/151 |
| 2011/0190693 | A1* | 8/2011 | Takatsuka | A61M 5/14546 340/815.4 |
| 2013/0281965 | A1 | 10/2013 | Kamen et al. | |
| 2019/0351132 | A1* | 11/2019 | Pippin | A61M 5/14566 |
| 2021/0236719 | A1* | 8/2021 | Peterson | A61M 5/1456 |

FOREIGN PATENT DOCUMENTS

| | | |
|---|---|---|
| EP | 2345441 A1 | 7/2011 |
| EP | 3135328 A1 | 3/2017 |

OTHER PUBLICATIONS

International Search Report and Written Opinion for Application No. PCT/US2020/043912, dated Sep. 24, 2020, 15 pages.

* cited by examiner

*Primary Examiner* — Emily L Schmidt
(74) *Attorney, Agent, or Firm* — Morgan, Lewis & Bockius LLP

(57) ABSTRACT

Syringe pumps are described herein. A syringe pump is disclosed comprising a syringe pump body, a flange clamp and a sensing switch. The syringe pump body defining a syringe body recess and a syringe plunger recess, wherein the syringe body recess and the syringe plunger recess are configured to cooperatively receive a syringe. The flange clamp is coupled to a mating surface of the syringe pump body disposed between the syringe body recess and the syringe plunger recess, wherein the flange clamp is configured to be spaced apart from the mating surface to receive a syringe flange of the syringe. The sensing switch extends through the mating surface, wherein the sensing switch is configured to be in a closed state when the flange clamp is in contact with the sensing switch and in an open state when the flange clamp is spaced apart from the sensing switch.

19 Claims, 4 Drawing Sheets

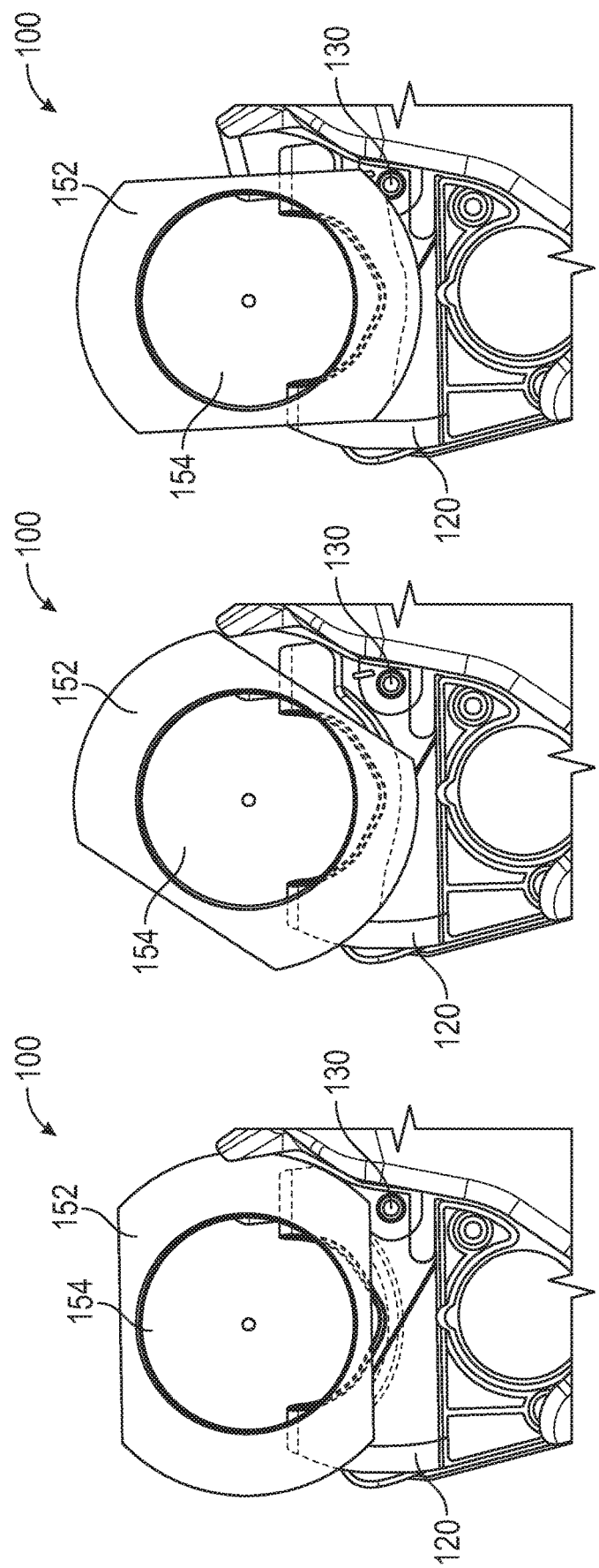

SYRINGE PUMP WITH FLANGE CLAMP SENSOR

RELATED APPLICATIONS

This application claims priority to U.S. Provisional Application Ser. No. 62/879,950, filed, Jul. 29, 2019, entitled "SYRINGE PUMP WITH FLANGE CLAMP SENSOR," which is incorporated by reference herein in its entirety.

FIELD OF THE INVENTION

The present disclosure generally relates to syringe pumps, and, in particular, to syringe pumps with a flange clamp sensor.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, a syringe. In some applications, medical fluid can be administered from the syringe by utilizing a syringe pump. During operation, the syringe pump can precisely actuate the syringe to control the amount of medical fluid administered.

In some applications, a syringe may be improperly loaded or aligned within the syringe pump, preventing the controlled administration of medical fluid.

SUMMARY

The disclosed subject matter relates to syringe pumps. In certain embodiments, a syringe pump is disclosed comprising a syringe pump body, a flange clamp and a sensing switch. The syringe pump body defining a syringe body recess and a syringe plunger recess, wherein the syringe body recess and the syringe plunger recess are configured to cooperatively receive a syringe. The flange clamp is coupled to a mating surface of the syringe pump body disposed between the syringe body recess and the syringe plunger recess, wherein the flange clamp is configured to be spaced apart from the mating surface to receive a syringe flange of the syringe. The sensing switch extends through the mating surface, wherein the sensing switch is configured to be in a closed state when the flange clamp is in contact with the sensing switch and in an open state when the flange clamp is spaced apart from the sensing switch.

In certain embodiments, a method comprises providing a syringe pump configured to actuate a syringe, wherein the syringe pump comprises a syringe body recess and a syringe plunger recess, depressing a sensing switch with a flange clamp to place the sensing switch in a closed state, wherein the flange clamp is coupled to a mating surface and the mating surface is disposed between the syringe body recess and the syringe plunger recess, and preventing actuation of the syringe via the syringe pump in response to the closed state of the sensing switch.

In certain embodiments, a syringe pump assembly comprises a syringe including a syringe body defining a syringe port, a syringe flange extending from the syringe body, and a syringe plunger extending into the syringe body, wherein the syringe plunger and the syringe body define a volume in fluid communication with the syringe port, and a syringe pump. The syringe pump comprises a syringe pump body, a flange clamp, and a sensing switch. The syringe pump body defines a syringe body recess and a syringe plunger recess, wherein the syringe body recess and the syringe plunger recess receive the syringe. The flange clamp couples to a mating surface of the syringe pump body disposed between the syringe body recess and the syringe plunger recess, wherein the syringe flange is disposed between the mating surface and the flange clamp. The sensing switch extends through the mating surface, wherein the sensing switch is configured to be in an open state when the syringe flange is disposed between the mating surface and the flange clamp.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 6A-6C are partial side views of the syringe pump of FIG. 1 with syringe in various orientations, in accordance with various aspects of the present disclosure.

DETAILED DESCRIPTION

Figure 1:
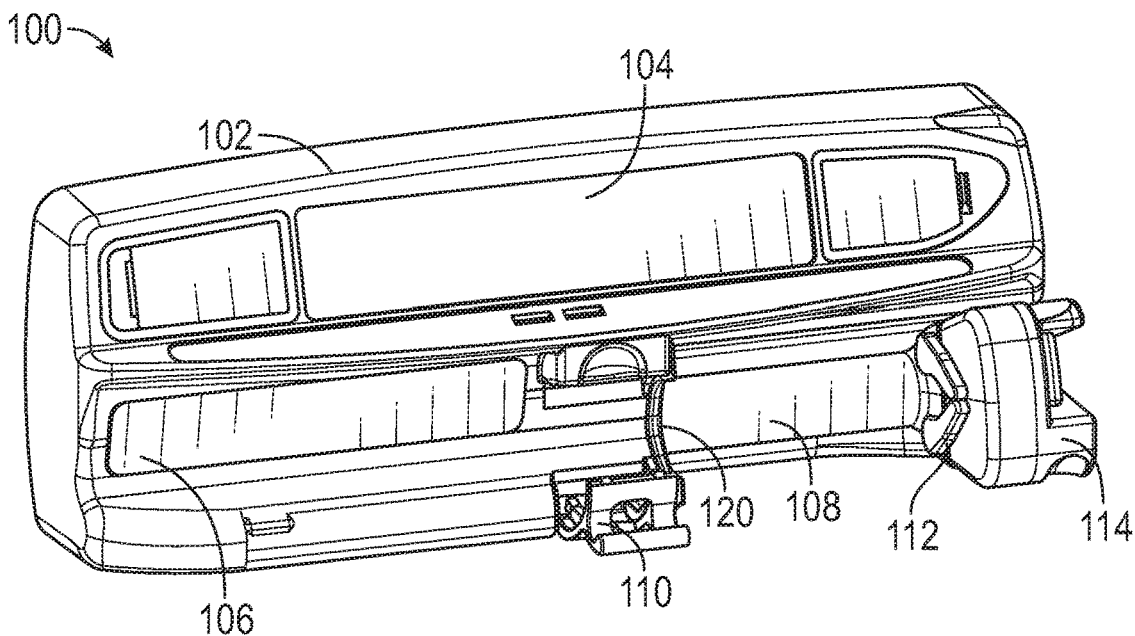
FIG. 1 is a perspective view of a syringe pump, in accordance with various aspects of the present disclosure.

The disclosed syringe pump incorporates a sensing switch to determine if a syringe is properly disposed within the syringe pump. The sensing switch can be in a closed state when a syringe flange is not within the flange clamp and can be in an open state when the syringe flange is within the flange clamp. By sensing the syringe flange within the flange clamp, the syringe pump can reliably detect the correct installation of the syringe and allow for precise administration of medical fluid.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to sensing a position of the syringe within the syringe pump, it is to be understood that this description is only an example of usage and does not limit the scope of the claims. Various aspects of the disclosed syringe pump may be used in any application where it is desirable to detect installation of an alignable component.

The disclosed syringe pump overcomes several challenges discovered with respect to certain conventional syringe pumps. One challenge with certain conventional syringe pumps is that certain conventional syringe pumps may include features that allow for syringes to be incorrectly installed or misloaded. Further, certain conventional syringe pumps may not effectively detect the misloading or incorrect installation of syringes within the syringe pump (e.g. wherein the syringe body, the syringe plunger, and/or the syringe flange are not properly inserted or oriented in the correct or as-designed way). Additional, certain conventional syringe pumps may include sensors that are not dust and/or water proof. Further, certain conventional syringe pumps may continue to administer medical fluid from a misloaded syringe without any alarm or warning to the clinician. Because undetected incorrect installation of syringes within the syringe pump may lead to over-infusion or under-infusion of medical fluids, the use of conventional syringe pumps is undesirable.

Therefore, in accordance with the present disclosure, it is advantageous to provide a syringe pump as described herein that allows for reliable and high confidence detection of misloaded syringes. Further, it is advantageous to provide a syringe pump as described herein that includes features that prevent incorrect installation or misloading of syringes. Additionally, it is advantageous to provide a syringe pump as described herein that includes sealing features that prevent the ingress of dust and/or water. The disclosed syringe pump provides a flange clamp and sensing switch that allows for reliable and high confidence detection of misloaded syringes and other advantages described herein.

An example of a syringe pump that allows for reliable and high confidence detection of misloaded syringes is now described.

FIG. 1 is a perspective view of a syringe pump 100, in accordance with various aspects of the present disclosure. In the depicted example, the syringe pump 100 can deliver or administer medical fluid from a syringe to a patient. The syringe pump 100 can actuate a plunger of a syringe to administer medical fluid from the syringe to the patient via tubing.

Prior to administration, the syringe pump 100 can receive the syringe within the body 102. In the depicted example, the body 102 can define a syringe body recess 106 to receive the body of the syringe and a syringe plunger recess 108 to receive the plunger portion of the syringe. Cooperatively, the syringe body recess 106 and the syringe plunger recess 108 receive the syringe. As can be appreciated, the syringe body recess 106 and/or the syringe plunger recess 108 can be shaped or include features to align the syringe within the body 102 of the syringe pump 100.

During operation, the syringe plunger can be depressed or actuated by a plunger actuator 114. The plunger actuator 114 can advance to depress or advance the syringe plunger relative to the syringe body to administer fluid. Optionally, the movement of the plunger actuator 114 can be controlled to administer a desired amount of medical fluid from the syringe. In some embodiments, a control panel 104 can be used to configure and control the syringe pump 100 and the advancement of the plunger actuator 114.

In some embodiments, a syringe can be secured to the syringe pump 100 with a syringe clamp assembly 110, a plunger clamp assembly 112, and/or a flange clamp 120. As described herein, the syringe clamp assembly 110, the plunger clamp assembly 112, and/or the flange clamp 120 can be used to retain and properly align or install the syringe within the syringe pump 100 such that the syringe body, the syringe plunger, and/or the syringe flange are properly inserted or oriented in the correct or as-designed way. By retaining and properly aligning the syringe within the syringe pump 100, the syringe pump 100 can accurately dispense medical fluid from the syringe without over or under infusion.

As described herein, the syringe pump 100 can include sensors or switches that are associated with the syringe clamp assembly 110, the plunger clamp assembly 112, and/or the flange clamp 120 to confirm the proper installation or alignment of the syringe within the syringe pump 100. Advantageously, such sensors can be utilized to provide an error or warning to the clinician either visually via the control panel 104 or audibly. In some embodiments, the sensors can be used with an interlock to prevent the operation of the syringe pump 100 if the sensors detect the syringe is not properly installed, preventing the inaccurate administration of medical fluid.

In the depicted example, a body of a syringe can be clamped to the syringe pump 100 by the syringe clamp assembly 110. In some embodiments, the syringe clamp assembly 110 comprises a semi-circular profile or any other profile that is complimentary to the shape of the body of the syringe to retain the syringe to the syringe pump 100.

In some embodiments, the syringe clamp assembly 110 is rotatable about a hinge or pivot to capture the syringe between the syringe clamp assembly 110 and the syringe body recess 106 in an engaged position. The syringe clamp assembly 110 can be rotated to a disengaged position to allow a syringe to be introduced or removed from the syringe pump 100.

As can be appreciated, the syringe clamp assembly 110 can be coupled to a sensor to detect the presence of the syringe body and to detect the size of the syringe. In some embodiments, the body sensor can be a rotary potentiometer that detects the rotary position of the syringe clamp assembly 110 to determine if the syringe clamp assembly 110 is in the engaged position or the disengaged position. Further, in the engaged position, the sensor can determine the size of the syringe from the rotary position of the syringe clamp assembly 110.

In the depicted example, a plunger of a syringe can be secured to the plunger actuator 114 by the plunger clamp assembly 112. In some embodiments, the plunger clamp assembly 112 can include a plurality of arms that extend from pivots coupled to the plunger clamp assembly 112. The arms of the plunger clamp assembly 112 can be spaced apart from a surface of the plunger actuator 114 to allow a portion of the plunger to fit therebetween.

In some embodiments, the plunger clamp assembly 112 includes one or more rotatable arms to capture an end of the plunger of the syringe between the plunger clamp assembly 112 and a surface of the plunger actuator 114 in a closed position. The arms of the plunger clamp assembly 112 can be moved or rotated to an open position to allow the plunger of the syringe to be disengaged from the plunger actuator 114 and/or the syringe pump 100 generally.

As can be appreciated, the plunger clamp assembly 112 can be coupled to one or more sensors to detect the presence of the syringe plunger. In some embodiments, the sensor can detect the position of the arms of the plunger clamp assembly 112 to determine if the plunger clamp assembly is in an open or closed position to determine if the syringe is properly clamped.

In the illustrated embodiment, a flange of a syringe by be secured to the body 102 by the flange clamp 120. In some embodiments, the flange clamp 120 includes a resilient or deformable body to capture a portion of the syringe flange between the flange clamp 120 and a mating surface of the body 102. As can be appreciated, the flange clamp 120 can be resiliently urged toward the body 102 to clamp or retain the syringe flange therebetween. The flange clamp 120 can be further spaced apart from the body 102 to allow the syringe flange to be inserted prior to operation or removed.

As described herein, the flange clamp 120 can be coupled to a sensing switch to detect the presence, alignment, and/or engagement of the syringe flange. In some embodiments, the sensing switch can detect the position of the flange clamp 120 to determine if the syringe flange is properly clamped therein.

Advantageously, by utilizing the flange clamp 120 with a sensing switch, the syringe pump 100 may be able to detect scenarios wherein a syringe is clamped to the syringe clamp assembly 110 and the plunger clamp assembly 112 but the syringe flange is not clamped to the flange clamp 120 due to rotational misalignment, tilting, axial misalignment, or if a clinician fits the syringe flange into an incorrect gap of the syringe pump 100. By utilizing the flange clamp 120 with the sensing switch, the syringe pump 100 can prevent under-infusion, over-infusion, and incorrect identification of syringe sizes.

Figure 2:
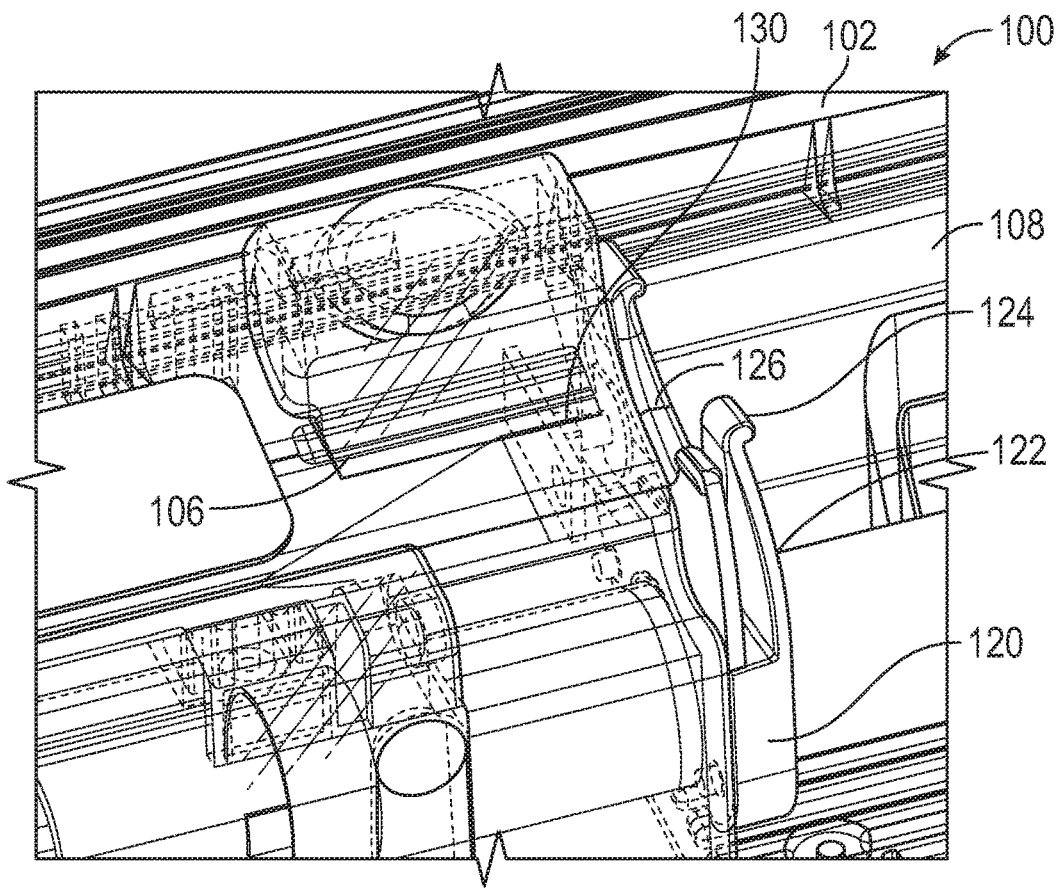
FIG. 2 is a detail perspective view of the syringe pump of FIG. 1 with certain elements shown in hidden lines, in accordance with various aspects of the present disclosure.
Figure 3:
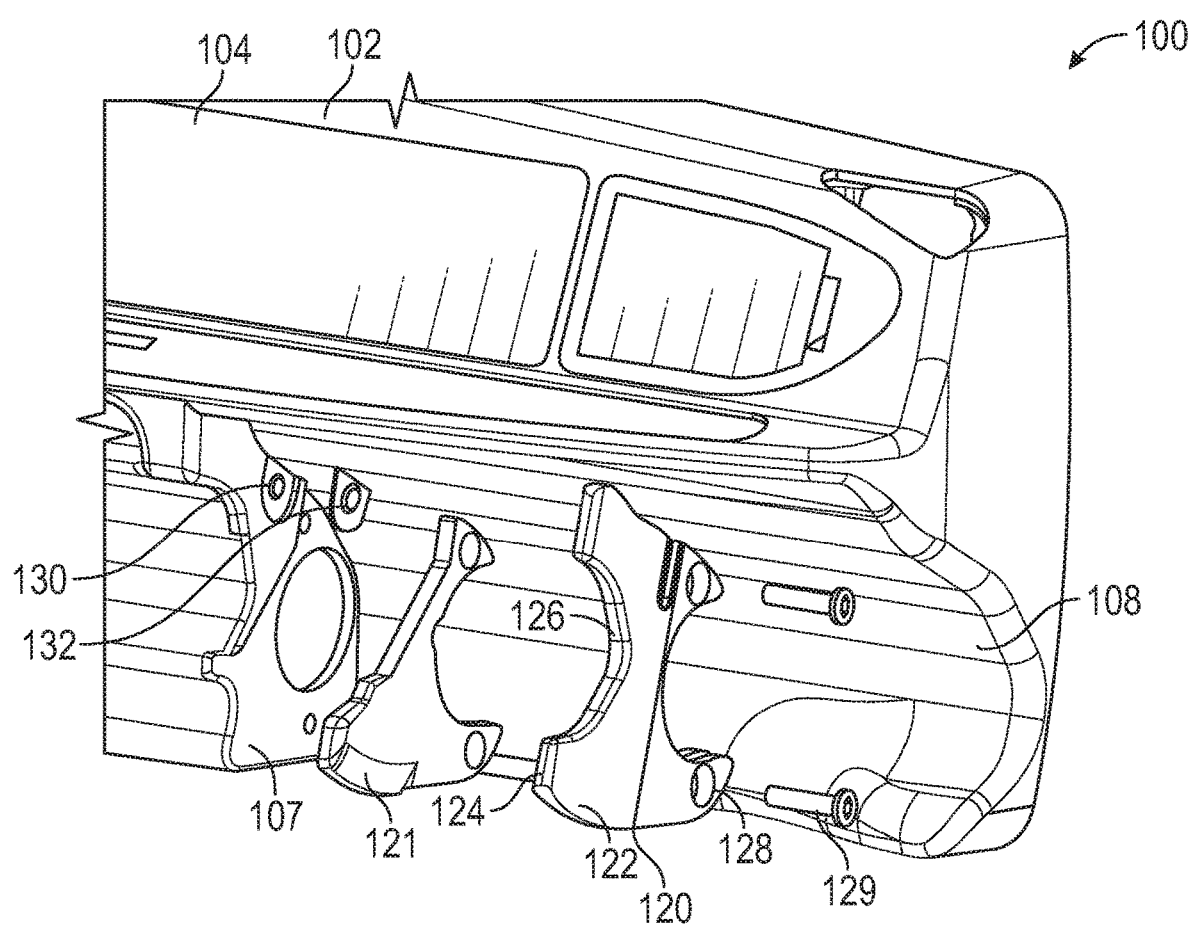
FIG. 3 is a detail exploded view of the syringe pump of FIG. 1, in accordance with various aspects of the present disclosure.
Figure 4:
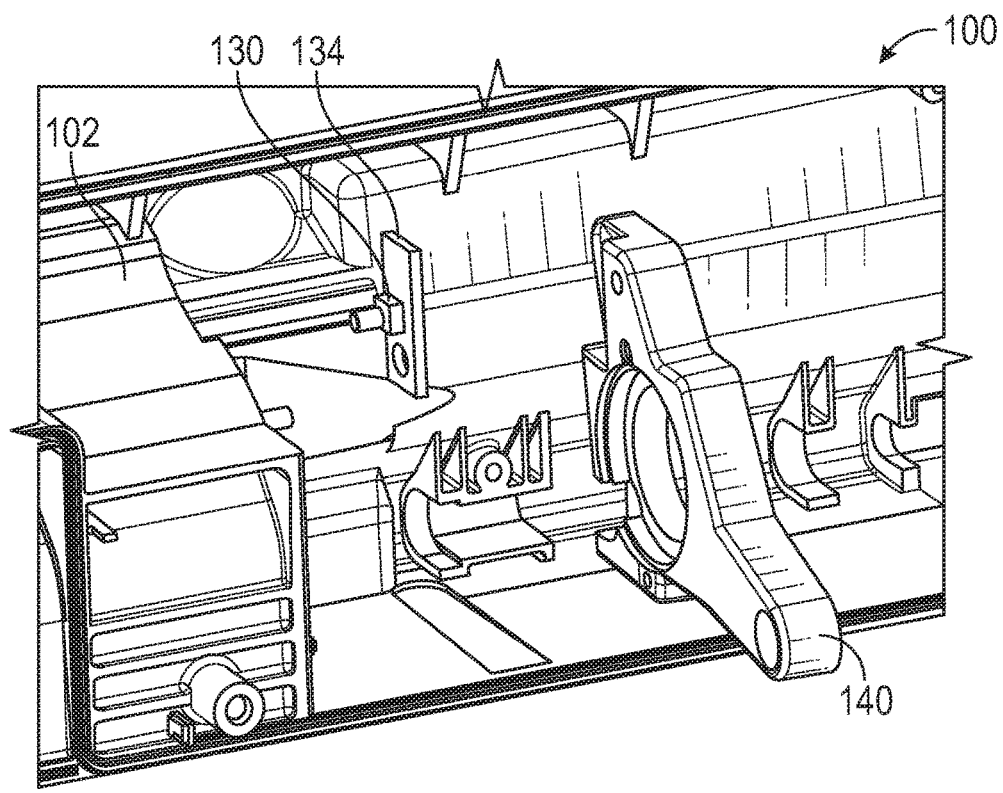
FIG. 4 is a reverse perspective view of the syringe pump of FIG. 1, in accordance with various aspects of the present disclosure.

FIG. 2 is a detail perspective view of the syringe pump 100 of FIG. 1 with certain elements shown in hidden lines, in accordance with various aspects of the present disclosure. FIG. 3 is a detail exploded view of the syringe pump 100 of FIG. 1, in accordance with various aspects of the present disclosure. FIG. 4 is a reverse perspective view of the syringe pump of FIG. 1, in accordance with various aspects of the present disclosure. With reference to FIGS. 2-4, the flange clamp 120 can facilitate insertion or engagement of the syringe flange and allow for reliable detection of proper insertion of the syringe within the syringe pump 100. In the depicted example, the flange clamp 120 can deflect when a syringe flange is inserted between the flange clamp 120 and a mating surface. The deflection of the flange clamp 120 can release the switch assembly 130 to an open state to allow the syringe pump 100 to detect the presence of the syringe flange.

In some embodiments, the flange clamp 120 is disposed between the syringe body recess 106 and the syringe plunger recess 108. As illustrated, the flange clamp 120 can be coupled to a mating surface 107 defined between the syringe body recess 106 and the syringe plunger recess 108. In some embodiments, fasteners 129 can pass through holes 128 formed through the flange clamp 120 to secure the flange clamp 120 to the body 102. In some embodiments, the fasteners 129 can engage the bearing block 140 disposed on the opposite side of the mating surface 107. In some embodiments, portions of the flange clamp 120 are spaced apart from the mating surface 107 by a spacer 121.

In the depicted example, the flange clamp 120 can include one or more clamp extensions 122 extending from the main body of the flange clamp 120. The clamp extensions 122 can be deflectable or deformable to receive and retain the syringe flange. Optionally, clamp ends 124 of the clamp extensions 122 can have rounded ends to locate the syringe flange between the clamp extensions 122 and the mating surface 107.

As illustrated, the clamp extensions 122 can define a plunger slot 126 within the flange clamp 120. The clamp extensions 122 can be configured to extend on either side of a syringe plunger to allow the syringe to be properly aligned within the syringe pump 100.

Advantageously, the construction of the flange clamp 120 can facilitate proper insertion of the syringe flange into the flange clamp 120. Further, the single-piece construction of the flange clamp 120 can prevent insertion of the syringe flange into an unintended gap or void of the syringe pump 100. In some embodiments, the flange clamp 120 can be formed of a material of a contrasting color to the body 102 to visually indicate the insertion area of the flange clamp 120.

As illustrated, the switch assembly 130 can be operatively coupled to the flange clamp 120 to detect the presence, alignment, and/or engagement of the syringe flange in response to the movement or deflection of the flange clamp 120. In some embodiments, the switch assembly 130 can extend through the mating surface 107 to sense the position of the flange clamp 120. As can be appreciated, the switch assembly 130 can be positioned wherein the switch assembly 130 is in a closed state when no syringe flange is inserted into the flange clamp 120 and the flange clamp 120 is in a resting position, and the switch assembly 130 is an open state when a syringe flange is inserted, deflecting or spacing apart the flange clamp 120 from the mating surface 107 and the switch assembly 130.

Therefore, during operation, when no syringe flange is inserted, the switch assembly 130 may be in a closed state, indicating that no syringe flange has been properly inserted. When the syringe flange is inserted, the flange clamp 120 may be sufficiently spaced apart from the switch assembly 130 and the mating surface 107 to indicate that the syringe flange has been properly inserted.

As can be appreciated, detection of the syringe flange via the switch assembly 130 can be based on the deflection of the flange clamp 120. In some applications, as little as 0.25 mm nominal deflection can be detected, allowing any size of syringe (and syringe flange) to be detected within the flange clamp 120.

In some embodiments, portions of the switch assembly 130 can be disposed on a PCB 134. Optionally, the PCB 134 can be mounted to the bearing block 140. In some embodiments, the switch assembly 130 can be covered with a sealing label 132. The sealing label 132 can prevent the ingress of water, dirt, dust, or other contaminants into the switch assembly 130. The sealing label 132 can be formed from an elastomeric or other resilient material.

Optionally, other suitable sensors can be used in place of switch assembly 130. For example, a magnet and hall sensor can be used to detect the position of the flange clamp 120. In some embodiments, a magnet can be attached to the flange clamp 120, wherein a hall sensor disposed within the body 102 can detect the deflection of the flange clamp 120 when a syringe flange is inserted, as described above.

Figure 5:
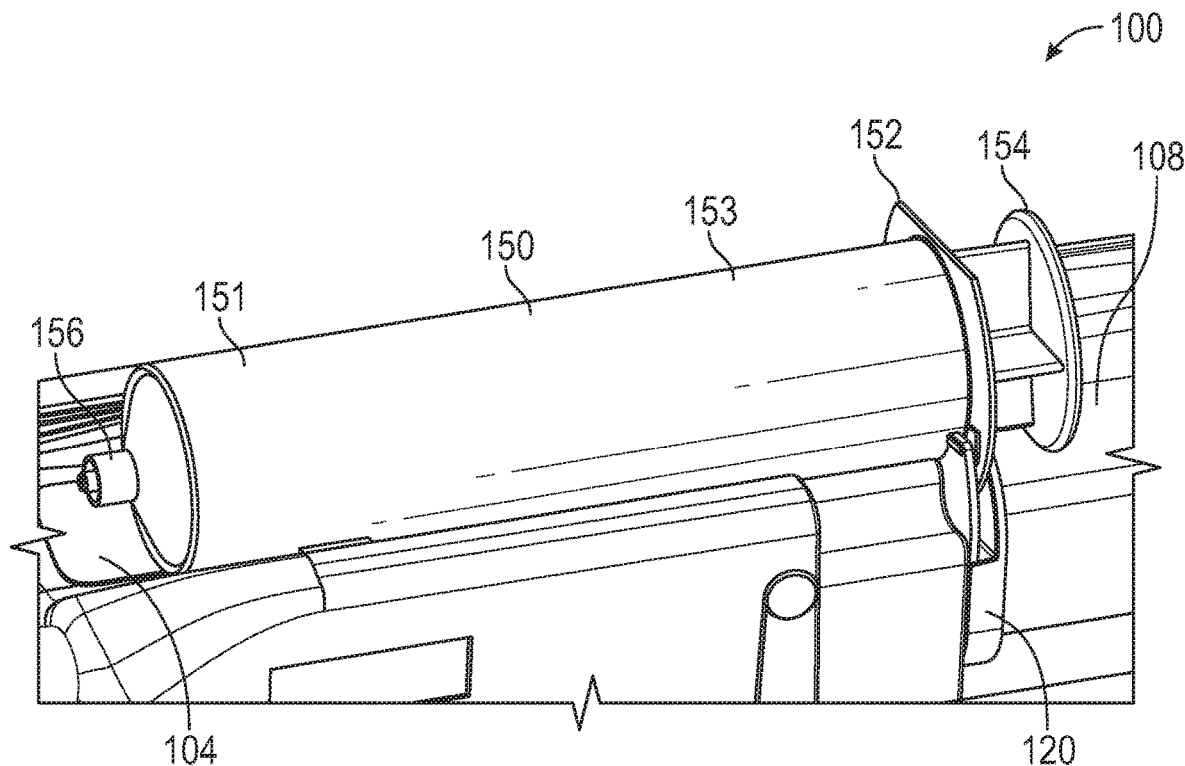
FIG. 5 is a detail perspective view of the syringe pump of FIG. 1 with a syringe, in accordance with various aspects of the present disclosure.

FIG. 5 is a detail perspective view of the syringe pump 100 of FIG. 1 with a syringe 150, in accordance with various aspects of the present disclosure. The syringe 150 includes a syringe body 151 and a syringe plunger 154 extending into the syringe body 151 defining a volume 153. The syringe plunger 154 can be advanced by the syringe pump 100 to allow medical fluid to be administered from the syringe port 156.

In the depicted example, the syringe 150 is aligned and inserted into the syringe pump 100. As shown, the syringe flange 152 extending from the syringe body 151 is engaged within the flange clamp 120. As discussed, upon inserting the syringe flange 152 within the flange clamp 120, the switch assembly can detect the proper insertion of the syringe 150 and permit operation of the syringe pump 100.

FIGS. 6A-6C are partial side views of the syringe pump 100 of FIG. 1 with syringe 150 in various orientations, in accordance with various aspects of the present disclosure. As can be appreciated, regardless of the rotational orientation of the syringe flange 152, the switch assembly 130 can effectively detect the syringe flange 152 correctly installed within the flange clamp 120.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various examples of aspects of the disclosure are described below as clauses for convenience. These are provided as examples, and do not limit the subject technology.

Clause 1. A syringe pump comprising: a syringe pump body defining a syringe body recess and a syringe plunger recess, wherein the syringe body recess and the syringe plunger recess are configured to cooperatively receive a syringe; a flange clamp coupled to a mating surface of the syringe pump body disposed between the syringe body recess and the syringe plunger recess, wherein the flange clamp is configured to be spaced apart from the mating surface to receive a syringe flange of the syringe; and a sensing switch extending through the mating surface, wherein the sensing switch is configured to be in a closed state when the flange clamp is in contact with the sensing switch and in an open state when the flange clamp is spaced apart from the sensing switch.

Clause 2. The syringe pump of Clause 1, further comprising: a syringe clamp assembly coupled to the syringe pump body, wherein the syringe clamp assembly is rotatable to retain the syringe within the syringe body recess.

Clause 3. The syringe pump of Clause 2, further comprising a body sensor coupled to the syringe clamp assembly and configured to detect a rotary position of the syringe clamp assembly.

Clause 4. The syringe pump of Clause 1, further comprising: a plunger actuator disposed at least partially within the syringe plunger recess, wherein the plunger actuator is configured to actuate a syringe plunger of the syringe.

Clause 5. The syringe pump of Clause 4, further comprising: a plunger clamp assembly coupled to the plunger actuator, wherein the plunger clamp assembly is movable to retain the syringe within the syringe plunger recess.

Clause 6. The syringe pump of Clause 5, further comprising a plunger sensor coupled to the plunger clamp assembly and configured to detect a position of the plunger clamp assembly.

Clause 7. The syringe pump of Clause 1, wherein a clamp extension extends from the flange clamp, wherein the clamp extension is configured to deflect away from the mating surface to receive the syringe flange of the syringe.

Clause 8. The syringe pump of Clause 7, wherein the clamp extension comprises a rounded clamp end.

Clause 9. The syringe pump of Clause 7, wherein the clamp extension defines at least a portion of a plunger slot through the flange clamp, the plunger slot configured to allow a syringe body of the syringe to pass therethrough.

Clause 10. The syringe pump of Clause 1, wherein the flange clamp is coupled to the syringe pump body with a fastener.

Clause 11. The syringe pump of Clause 10, wherein the fastener engages a bearing block disposed within the syringe pump body.

Clause 12. The syringe pump of Clause 1, further comprising a sealing label disposed over at least a portion of the sensing switch, wherein the sealing label comprises an elastomer.

Clause 13. A method comprising: providing a syringe pump configured to actuate a syringe, wherein the syringe pump comprises a syringe body recess and a syringe plunger recess; depressing a sensing switch with a flange clamp to place the sensing switch in a closed state, wherein the flange clamp is coupled to a mating surface and the mating surface is disposed between the syringe body recess and the syringe plunger recess; and preventing actuation of the syringe via the syringe pump in response to the closed state of the sensing switch.

Clause 14. The method of Clause 13, further comprising: disposing the syringe within the syringe pump; aligning a syringe body of the syringe with the syringe body recess of the syringe pump; aligning a syringe plunger of the syringe with the syringe plunger recess of the syringe pump; introducing a syringe flange between the flange clamp and the mating surface; spacing the flange clamp away from the sensing switch extending through the mating surface to place the sensing switch in an open state; and permitting actuation of the syringe via the syringe pump in response to the open state of the sensing switch.

Clause 15. The method of Clause 13, further comprising: rotating a syringe clamp assembly to a disengaged position; and preventing actuation of the syringe via the syringe pump in response to the disengaged position of the syringe clamp assembly.

Clause 16. The method of Clause 15, further comprising: aligning a syringe body with the syringe body recess; rotating the syringe clamp assembly to a engaged position to retain the syringe body within the syringe body recess; and permitting actuation of the syringe via the syringe pump in response to the engaged position of the syringe clamp assembly.

Clause 17. The method of Clause 13, further comprising: moving a plunger clamp assembly to an open position; and preventing actuation of the syringe via the syringe pump in response to the open position of the plunger clamp assembly.

Clause 18. The method of Clause 17, further comprising: aligning a syringe plunger with the syringe plunger recess and a plunger actuator; moving the plunger clamp assembly to a closed position to retain the syringe plunger within the syringe plunger recess and to couple the syringe plunger to the plunger actuator; and permitting actuation of the syringe via the syringe pump in response to the closed position of the plunger clamp assembly.

Clause 19. A syringe pump assembly comprising: a syringe comprising: a syringe body defining a syringe port; a syringe flange extending from the syringe body; and a syringe plunger extending into the syringe body, wherein the syringe plunger and the syringe body define a volume in fluid communication with the syringe port; and a syringe pump comprising: a syringe pump body defining a syringe body recess and a syringe plunger recess, wherein the syringe body recess and the syringe plunger recess receive the syringe; a flange clamp coupled to a mating surface of the syringe pump body disposed between the syringe body recess and the syringe plunger recess, wherein the syringe flange is disposed between the mating surface and the flange clamp; and a sensing switch extending through the mating surface, wherein the sensing switch is configured to be in an open state when the syringe flange is disposed between the mating surface and the flange clamp.

Clause 20. The syringe pump assembly of Clause 19, wherein the sensing switch is configured to be in a closed state when the syringe flange is not disposed between the mating surface and the flange clamp.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A syringe pump comprising:
    a syringe pump body defining a syringe body recess and a syringe plunger recess, wherein the syringe body recess and the syringe plunger recess are configured to cooperatively receive a syringe;
    a flange clamp coupled to a mating surface of the syringe pump body disposed between the syringe body recess and the syringe plunger recess, wherein the flange clamp is configured to be spaced apart from the mating surface to receive a syringe flange of the syringe and the flange clamp is coupled to the syringe pump body with a fastener that extends through the flange clamp to engage a bearing block disposed within the syringe pump body;
a sensing switch extending through the mating surface, wherein the sensing switch is configured to be in a closed state when the flange clamp is in contact with the sensing switch and in an open state when the flange clamp is spaced apart from the sensing switch, wherein a portion of the sensing switch is coupled to the bearing block; and
a spacer disposed between the flange clamp and the mating surface.

2. The syringe pump of claim 1, further comprising:
a syringe clamp assembly coupled to the syringe pump body, wherein the syringe clamp assembly is rotatable to retain the syringe within the syringe body recess.

3. The syringe pump of claim 2, further comprising a body sensor coupled to the syringe clamp assembly and configured to detect a rotary position of the syringe clamp assembly.

4. The syringe pump of claim 1, further comprising:
a plunger actuator disposed at least partially within the syringe plunger recess, wherein the plunger actuator is configured to actuate a syringe plunger of the syringe.

5. The syringe pump of claim 4, further comprising:
a plunger clamp assembly coupled to the plunger actuator, wherein the plunger clamp assembly is movable to retain the syringe within the syringe plunger recess.

6. The syringe pump of claim 5, further comprising a plunger sensor coupled to the plunger clamp assembly and configured to detect a position of the plunger clamp assembly.

7. The syringe pump of claim 1, wherein a clamp extension extends from the flange clamp, wherein the clamp extension is configured to deflect away from the mating surface to receive the syringe flange of the syringe.

8. The syringe pump of claim 7, wherein the clamp extension comprises a rounded clamp end.

9. The syringe pump of claim 7, wherein the clamp extension is configured to extend along either side of the syringe flange defining at least a portion of a plunger slot through the flange clamp, the plunger slot configured to align the syringe relative to the syringe pump and to allow the syringe plunger of the syringe to pass therethrough.

10. The syringe pump of claim 1, further comprising a sealing label disposed over at least a portion of the sensing switch, wherein the sealing label comprises an elastomer.

11. The syringe pump of claim 1, wherein the portion of the sensing switch is disposed on a printed circuit board mounted to the bearing block.

12. A method comprising:
providing a syringe pump configured to actuate a syringe, wherein the syringe pump comprises a syringe body recess and a syringe plunger recess;
depressing a sensing switch with a flange clamp to place the sensing switch in a closed state, wherein the flange clamp is coupled to a mating surface and the mating surface is disposed between the syringe body recess and the syringe plunger recess, wherein the flange clamp is coupled to the syringe pump with a fastener that extends through the flange clamp to engage a bearing block disposed within the syringe pump body and a portion of the sensing switch is coupled to the bearing block and a spacer disposed between the flange clamp and the mating surface; and
preventing actuation of the syringe via the syringe pump in response to the closed state of the sensing switch.

13. The method of claim 12, further comprising:
disposing the syringe within the syringe pump;
aligning a syringe body of the syringe with the syringe body recess of the syringe pump;
aligning a syringe plunger of the syringe with the syringe plunger recess of the syringe pump;
introducing a syringe flange between the flange clamp and the mating surface;
spacing the flange clamp away from the sensing switch extending through the mating surface to place the sensing switch in an open state; and
permitting actuation of the syringe via the syringe pump in response to the open state of the sensing switch.

14. The method of claim 12, further comprising:
rotating a syringe clamp assembly to a disengaged position; and
preventing actuation of the syringe via the syringe pump in response to the disengaged position of the syringe clamp assembly.

15. The method of claim 14, further comprising:
aligning a syringe body with the syringe body recess;
rotating the syringe clamp assembly to an engaged position to retain the syringe body within the syringe body recess; and
permitting actuation of the syringe via the syringe pump in response to the engaged position of the syringe clamp assembly.

16. The method of claim 12, further comprising:
moving a plunger clamp assembly to an open position; and
preventing actuation of the syringe via the syringe pump in response to the open position of the plunger clamp assembly.

17. The method of claim 16, further comprising:
aligning a syringe plunger with the syringe plunger recess and a plunger actuator;
moving the plunger clamp assembly to a closed position to retain the syringe plunger within the syringe plunger recess and to couple the syringe plunger to the plunger actuator; and
permitting actuation of the syringe via the syringe pump in response to the closed position of the plunger clamp assembly.

18. A syringe pump assembly comprising:
a syringe comprising:
a syringe body defining a syringe port; a syringe flange extending from the syringe body; and
a syringe plunger extending into the syringe body, wherein the syringe plunger and the syringe body define a volume in fluid communication with the syringe port; and
a syringe pump comprising:
a syringe pump body defining a syringe body recess and a syringe plunger recess, wherein the syringe body recess and the syringe plunger recess receive the syringe;
a flange clamp coupled to a mating surface of the syringe pump body disposed between the syringe body recess and the syringe plunger recess, wherein the syringe flange is disposed between the mating surface and the flange clamp and the flange clamp is coupled to the syringe pump body with a fastener that extends through the flange clamp to engage a bearing block disposed within the syringe pump body;
a sensing switch extending through the mating surface, wherein the sensing switch is configured to be in an open state when the syringe flange is disposed between the mating surface and the flange clamp and the sensing switch is configured to be in a closed state when the flange clamp is in contact with the sensing switch, wherein a portion of the sensing switch is coupled to the bearing block; and a spacer disposed between the flange clamp and the mating surface.

19. The syringe pump assembly of claim 18, wherein the sensing switch is configured to be in a closed state when the syringe flange is not disposed between the mating surface and the flange clamp.

* * * * *